United States Patent
Brown et al.

(10) Patent No.: US 7,893,876 B2
(45) Date of Patent: Feb. 22, 2011

(54) SYSTEM AND METHOD FOR DETERMINING LOCATIONS OF MEDICAL DEVICES

(75) Inventors: Houston Brown, Poway, CA (US); Robert Butterfield, Poway, CA (US); Daniel Brightwell, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 290 days.

(21) Appl. No.: 11/933,992

(22) Filed: Nov. 1, 2007

(65) Prior Publication Data

US 2009/0115663 A1 May 7, 2009

(51) Int. Cl.
*G01S 3/02* (2006.01)
(52) U.S. Cl. ..................................... 342/465
(58) Field of Classification Search .......... 342/465
See application file for complete search history.

(56) References Cited

U.S. PATENT DOCUMENTS

| 6,371,416 | B1* | 4/2002 | Hawthorne | 246/122 R |
|---|---|---|---|---|
| 7,106,717 | B2* | 9/2006 | Rousseau et al. | 370/338 |
| 2003/0016122 | A1 | 1/2003 | Petrick | |
| 2005/0135306 | A1 | 6/2005 | McAllen et al. | |
| 2005/0137653 | A1 | 6/2005 | Friedman et al. | |
| 2005/0258956 | A1 | 11/2005 | Neuwirth | |
| 2006/0055536 | A1 | 3/2006 | Jackson | |
| 2006/0066450 | A1 | 3/2006 | Jackson | |
| 2006/0267833 | A1 | 11/2006 | Langford et al. | |
| 2006/0279427 | A1 | 12/2006 | Becker et al. | |
| 2007/0068089 | A1 | 3/2007 | Gallant et al. | |
| 2007/0083294 | A1* | 4/2007 | Bruno | 700/295 |
| 2007/0255111 | A1* | 11/2007 | Baldus et al. | 600/300 |

FOREIGN PATENT DOCUMENTS

| JP | 2003189353 | 7/2003 |
|---|---|---|
| WO | WO 9923623 | 5/1999 |
| WO | WO 0244865 | 6/2002 |
| WO | WO 2006105269 | 5/2006 |

OTHER PUBLICATIONS

International Search Report from PCT/US2008/081640, dated Aug. 28, 2009.

* cited by examiner

*Primary Examiner*—Thomas H Tarcza
*Assistant Examiner*—Harry Liu
(74) *Attorney, Agent, or Firm*—McDermott Will & Emery LLP

(57) ABSTRACT

The location of a medical device is determined by receiving one or more signals at the medical device transmitted by one or more beacons, respectively, at known locations. The one or more signals received at the medical device are sent from the medical device to a processor, which determines the location of the medical device based on the received one or more signals. One of the beacons may be a portable patient beacon, the location of which is determined when its signal is received by a medical device, the location of which was previously determined.

21 Claims, 5 Drawing Sheets

SYSTEM AND METHOD FOR DETERMINING LOCATIONS OF MEDICAL DEVICES

FIELD

The present disclosure relates generally to a system and method for determining a location of items, and more particularly, to a system and method for determining the locations of medical devices and/or patients in an institution, such as a medical facility.

BACKGROUND

It is known in the art to track movement and locations of items using human involvement, such as reading barcodes, or without human involvement, such as automatically detecting items that pass through a field such as an antenna. For example, US20050258956 discloses an RFID reader detecting a tag's emitted RF signal when the signal is within the range of the reader's emitted RF field. The reader detects the presence of an RFID tag by detecting its RF signal, and processes the received RF signal to accurately determine the unique identification code of the tag. However, such a conventional system only determines where an item has previously passed through and cannot determine where an item is currently.

Some conventional systems employ beacon transponders on the item to be tracked. These systems are capable of determining actual location of the item; however, the beacon transponders require substantial power consumption. These systems require a vast and costly installation of antennae and/or infrared (IR) detectors in a facility. The beacon transponders are costly and require considerable maintenance to replace the batteries, assuming the transponders can be located after the batteries die.

SUMMARY

The presently disclosed embodiments are directed to solving one or more of the problems presented in the prior art, described above, as well as providing additional features that will become readily apparent by reference to the following detailed description when taken in conjunction with the accompanying drawings.

Certain disclosed embodiments are directed to a method of determining a location of a medical device. The method comprises the steps of receiving one or more signals at the medical device transmitted by one or more beacons, respectively, at known locations; sending from the medical device the received one or more signals to a processor; and determining, by the processor, the location of the medical device based on the received one or more signals.

Certain disclosed embodiments are directed to a system for determining a location of a medical device. The system comprises one or more transmitting units at known locations to transmit one or more signals, respectively; a receiver at the medical device to receive the one or more signals; and a transceiver, communicatively coupled to the receiver, to send the received one or more signals to a processor, the processor determining the location of the medical device based on the received one or more signals.

Certain disclosed embodiments are directed to an apparatus for determining a location of one or more items within an institution. The apparatus comprises one or more beacons at known locations transmitting one or more signals, respectively; a receiver at an item receiving the one or more signals; a transceiver sending the received one or more signals to a processor, the processor determining the location of the medical item based on the received one or more signals; and portable patient beacon transmitting a signal received by the receiver, wherein the transceiver sends the signal to the processor to determine a location of the portable patient beacon, based on the determined location of the item.

Certain disclosed embodiments are directed to a method of determining a location of at least one item. The method comprises receiving one or more signals at an item transmitted by one or more beacons, respectively, at known locations; sending from the item the received one or more signals to a processor; and determining, by the processor, the location of the item based on the received one or more signals.

Of course, the present invention is not limited to the aforementioned embodiments, and other features of the embodiments will become apparent after review of the hereinafter set forth Brief Description of the Drawings, Detailed Description, and the Claims, or may be learned by practice of the invention.

BRIEF DESCRIPTION OF THE DRAWINGS

The foregoing aspects of the embodiments described herein will become more readily apparent by reference to the following detailed description when taken in conjunction with the accompanying drawings wherein.

DETAILED DESCRIPTION

Figure 1:
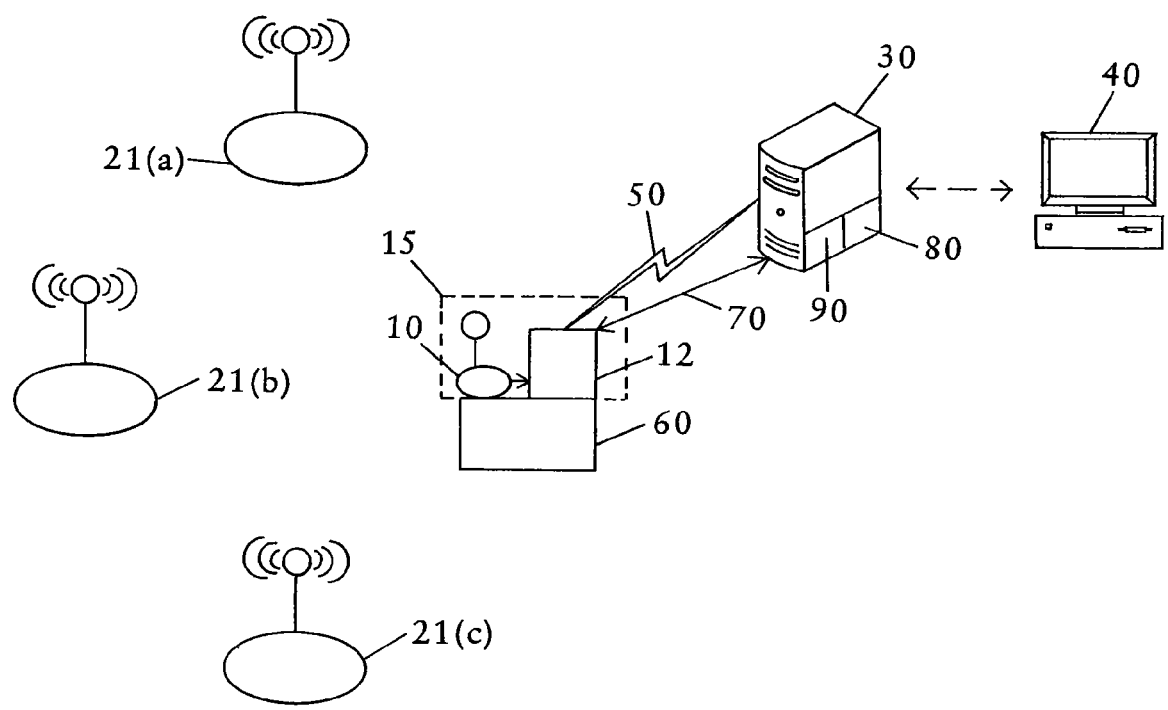
FIG. 1 is a graphical illustration of a system for determining a location of a medical device, according to disclosed embodiments.

Reference will now be made in detail to the presently disclosed embodiments, examples of which are illustrated in the accompanying drawings, wherein like reference numerals refer to like elements throughout.

FIG. 1 is a graphical illustration of a system for determining a location of a medical device, according to disclosed embodiments. In the exemplary embodiment depicted in FIG. 1, a medical device 60 is connected to a receiver 10 (e.g., an Alaris® Point of Care Unit (PCU)). It is noted that the disclosed embodiments are not limited to the receiver 10 being connected to the medical device 60, and the receiver 10 may alternatively be inside or within close proximity to the medical device 60. It is further noted that the medical device 60 may be any item or items for which a location is to be determined.

Transmitter beacons 21(a), 21(b) and 21(c) (hereinafter referred to as "beacons") periodically transmit a signal coded with a predetermined unique ID, corresponding to each of the beacons 21(a)-21(c) respectively. In the exemplary embodiment depicted in FIG. 1, three beacons 21(a)-21(c) are shown, but any number of beacons may be used. In certain embodiments, beacons 21(a)-21(c) are located at known locations within relatively small areas, such as a room, elevator, hallway, etc.

A server 30, for example, includes a memory 80, which stores the predetermined unique IDs associated with the respective beacons 21(a)-21(c), as well as their corresponding known locations. According to certain embodiments, beacons 21(a)-21(c) are reconfigurable, such that each beacon 21(a)-21(c) may be transported to another location, which would be stored in memory 80.

In certain embodiments, beacons 21(a)-21(c) employ a low-power transmitter along with a solar cell (not shown), and a storage device (not shown) for operation with low light intensity, to power the beacons 21(a)-21(c). In this manner, the beacons 21(a)-21(c) are positioned at any surface at any particular location without the need for wiring, and require minimal installation and/or maintenance. Alternatively, a battery or AC mains may be employed to power the beacons 21(a)-21(c). In certain embodiments, beacons 21(a)-21(c) transmit signals using a common Frequency Modulation (FM) signal, where only the strongest signal(s) (i.e., the signal(s) transmitted from proximate beacon(s)) will be received by the receiver 10.

The receiver 10 receives one or more signals transmitted by the beacons 21(a)-21(c). The receiver 10 is communicatively coupled to a transceiver 12, which communicates the received one or more signals to the server 30, via a wireless connection 50 (e.g., WiFi) or a hard-wired connection 70 (e.g., a local area network). According to certain embodiments, the transceiver 12 is a device previously incorporated into a local area network and/or wireless local area network, complying with IEEE 802.11 standards. However, any conventional transceiver 12 may be employed. As shown in the embodiment depicted in FIG. 1, the receiver 10 and transceiver 12 are located in one device package 15. It is noted, however, that the receiver 10 and transceiver 12 are not required physically connected or located within one device package 15.

A processor 90 within server 30 determines from which of the beacons 21(a)-21(c) a received signal was transmitted, based on a corresponding unique ID coded in the received signal and stored in memory 80. The corresponding unique ID is mapped in memory 80 to a specific grid location in an institution, for example. The processor 90 then determines the location of receiver 10, and thus the location of medical device 60, as being proximate the beacon(s) 21(a)-21(c) from which the received signal was transmitted.

In certain embodiments, the determined location of medical device 60 is displayed to a user via a user interface 40, which may be any conventional interface including hardware such as a touch screen, keypad, keyboard, point and click device, etc. According to certain embodiments, the user requests the location of the medical device 60 from the server 30, at which point the processor 90 of the server 30 determines the location of the medical device 60 based on the most recently received signals transmitted by the beacons 21(a)-21(c).

The memory 80 of the server 30 stores a record of previously determined locations of the medical device 60, so that the user can track movement of the medical device 60 and effectively predict a location of the medical device 60 if the receiver 10 loses contact with the server 30, for example. According to certain embodiments, the receiver 10 periodically powers up and communicates with transceiver 12 to send currently received signals from the beacons 21(a)-21(c) to the server 30, so that the memory 80 of the server 30 contains a continuous record of position information for the medical device 60. After communicating the currently received signals to transceiver 12, the receiver 10 shuts down in order to save power.

Figure 2:
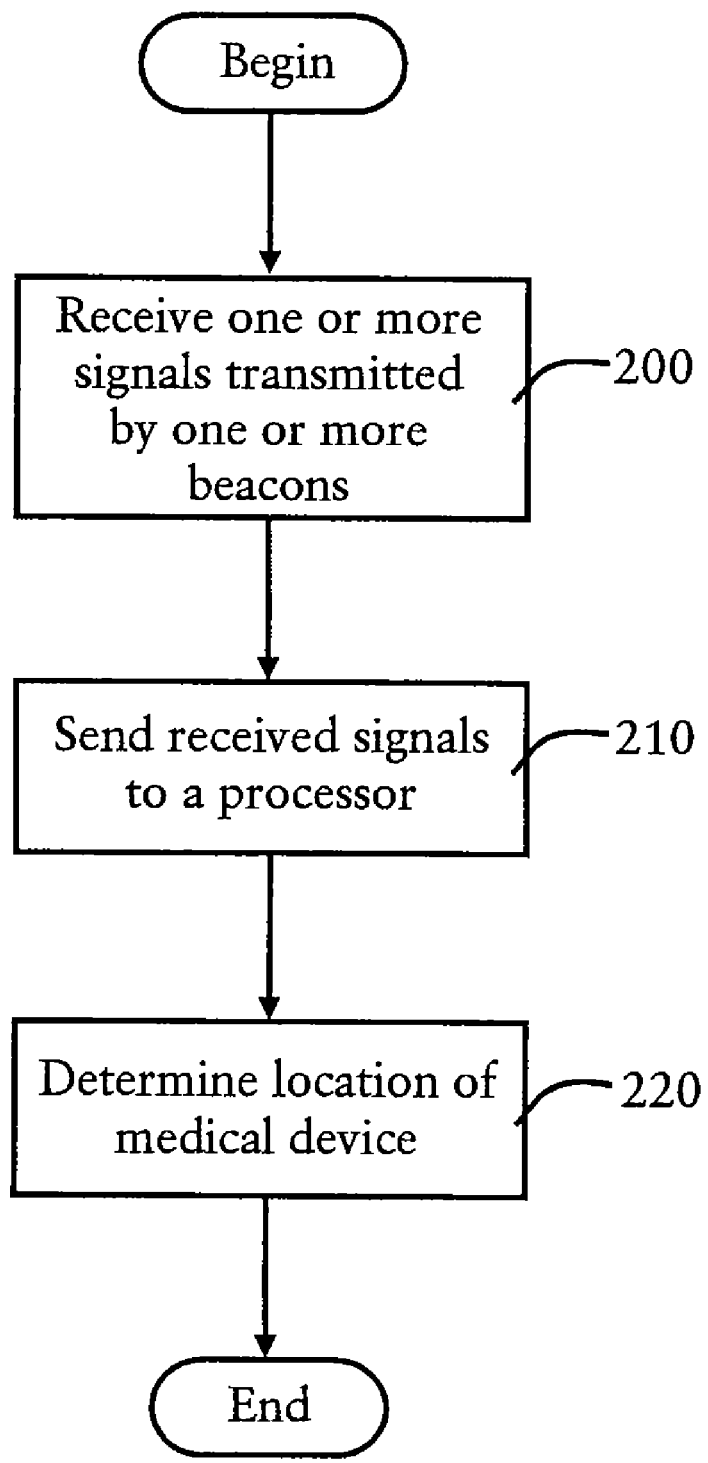
FIG. 2 is a flowchart illustrating a method of determining a location of items, according to disclosed embodiments.

FIG. 2 is a flowchart illustrating a method of determining a location of items (e.g., medical device 60), according to disclosed embodiments. At step 200 one or more signals transmitted by one or more beacons 21(a)-21(c), respectively, are received at the receiver 10, located at or connected to the medical device 60, for example, whose location is to be determined. Since the receiver 10 is located at or connected to the medical device 60, determining the location of the receiver 10 results in a determination of the location of the medical device 60.

From step 200, the process proceeds to step 210, where the receiver 10 communicates the received signals to transceiver 12, which sends the received signals to the server 30. From step 210, the process proceeds to step 220, where the processor 90 within server 30 determines the location of the receiver 10, and thus the medical device 60, based on the received signals. The processor 90 determines which one of the beacons 21(a)-21(c) transmitted the received signal(s), based on the unique ID coded in the received signal(s), and extracts the specific grid location of the corresponding one of the beacons 21(a)-21(c) from the memory 80. As a result, the processor 90 determines the location of the receiver 10, and thus the location of medical device 60, as being proximate the known location of the beacon(s) transmitting the received signal(s).

Figure 3:
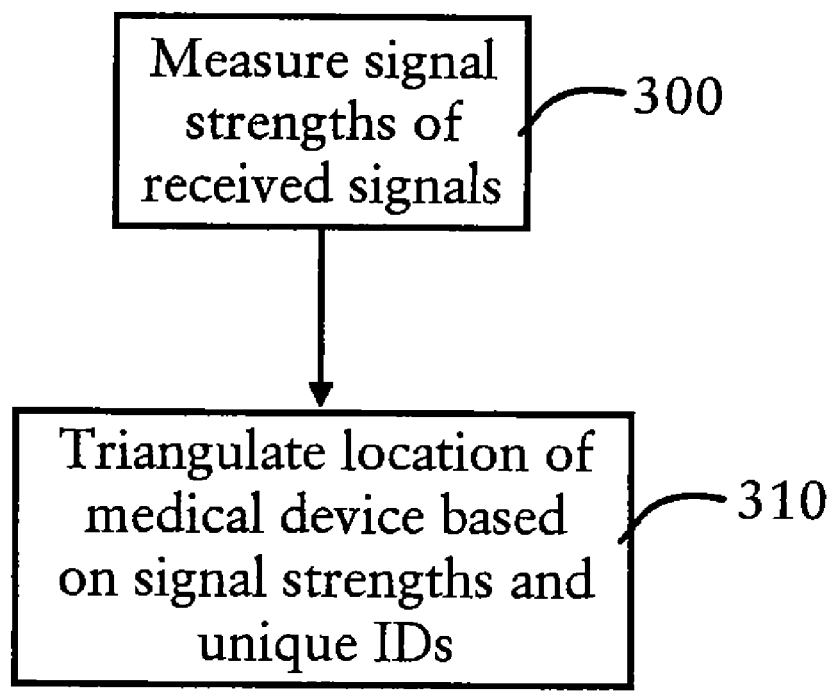
FIG. 3 is a flowchart illustrating a method of determining a location of a medical device based on one or more received signals, according to disclosed embodiments.

FIG. 3 is a flowchart illustrating a method of determining a location of a medical device 60 based on one or more received signals, according to disclosed embodiments. At step 300, the processor 90 within server 30 measures the signal strengths of a plurality of received signals transmitted by a plurality of respective beacons 21(a)-21(c).

From step 300, the process proceeds to step 310, where the processor 90 triangulates the location of the receiver 10, and thus the medical device 60, based on the signal strengths and the unique IDs of each the plurality of received signals. The processor 90 determines which one of the beacons 21(a)-21(c) corresponds to each received signal, based on the respective unique IDs of each of the plurality of received signals. Processor 90 determines that the receiver 10, and thus the medical device 60, is closer to a first beacon, with respect to a second beacon, when the signal received from the first beacon is stronger, since the strength of each of the plurality of received signals is proportional to its originating beacon's proximity to the receiver 10. Therefore, based on the signal strengths of each of the plurality of received signals, the processor 90 triangulates the location of the receiver 10, and thus the location of the medical device 60.

Figure 4:
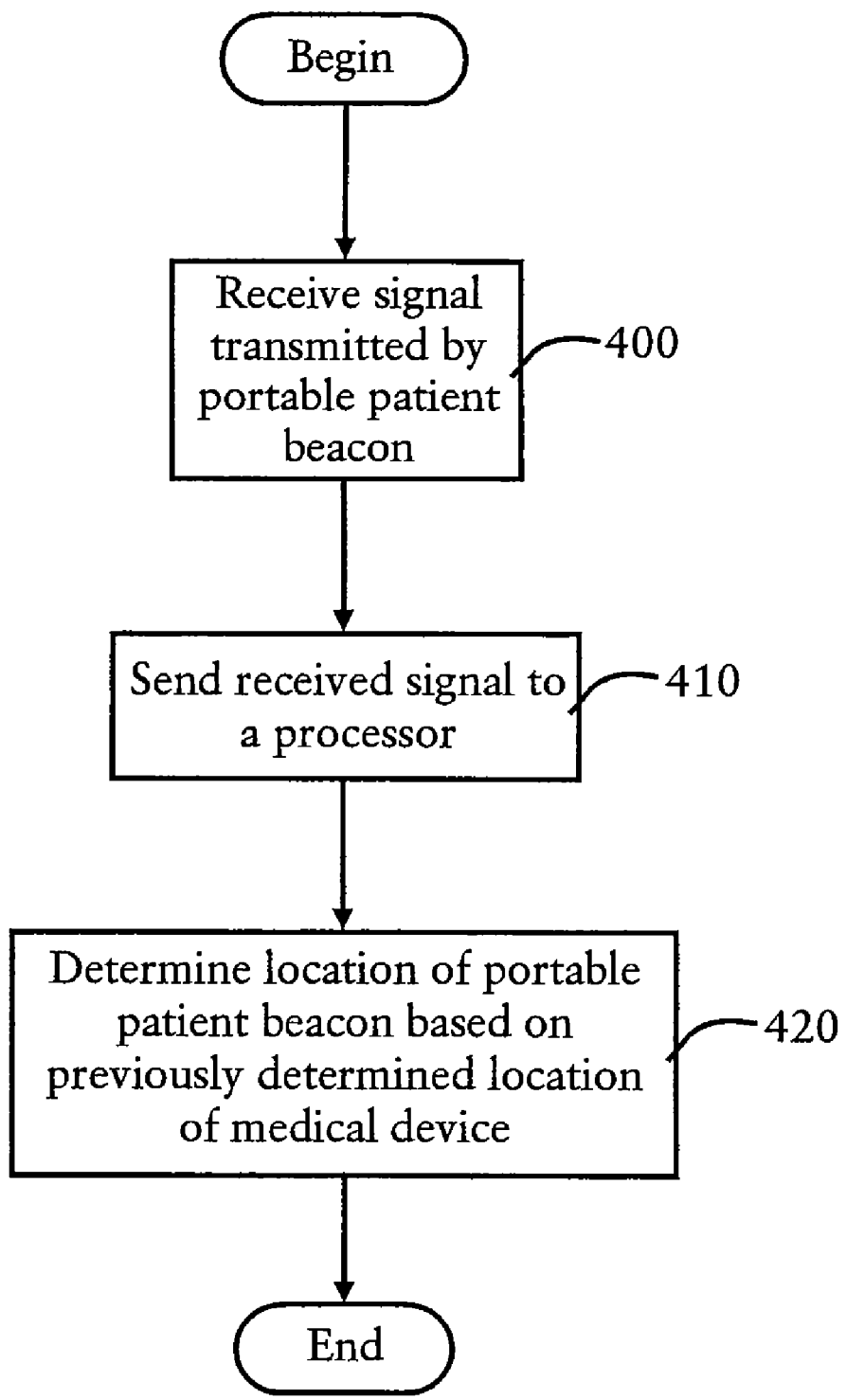
FIG. 4 is a flowchart illustrating a method of determining a location of a portable patient beacon, according to disclosed embodiments.

FIG. 4 is a flowchart illustrating a method of determining a location of a portable patient beacon, according to disclosed embodiments. FIG. 4 should be considered simultaneously with FIG. 5. After the location of the medical device 60 is determined, according to certain embodiments, the location of the medical device 60 is used to determine the location of a patient 100 (see FIG. 5) via determining a location of a portable patient beacon 21(d) located in proximity to the patient 100.

At step 400, the receiver 10 receives a signal transmitted by the portable patient beacon 21(d), and communicates the signal to transceiver 12. It is noted that the portable patient beacon 21(d) is configured in the same manner as beacons 21(a)-21(c), and a signal transmitted therefrom is coded with a predetermined unique ID corresponding to the patient 100 and is stored in the memory 80 of the server 30. According to certain embodiments, the portable patient beacon 21(d) transmits a low-power signal to limit its range, thereby allowing a precise location determination. Also, according to certain embodiments, the portable patient beacon 21(*d*) is powered by a battery (not shown) to last the stay of the patient 100, typically less than two weeks.

From step 400, the process proceeds to step 410, where the transceiver 12 sends the received signal from the portable patient beacon 21(*d*) to the server 30. As shown in FIG. 1, the transceiver 12 can send the received signal to the server 30 via either wireless connection 50 or hard-wired connection 70.

From step 410, the process proceeds to step 420, where the processor 90 determines the location of the portable patient beacon 21(*d*), and thus determines the location of the patient 100, based on the previously determined location of the medical device 60. That is, because the receiver 10 at the medical device 60 is in range of the portable patient beacon 21(*d*), the processor 90 deduces that the location of the portable patient beacon 21(*d*) (and patient 100) is proximate the medical device 60.

Figure 5:
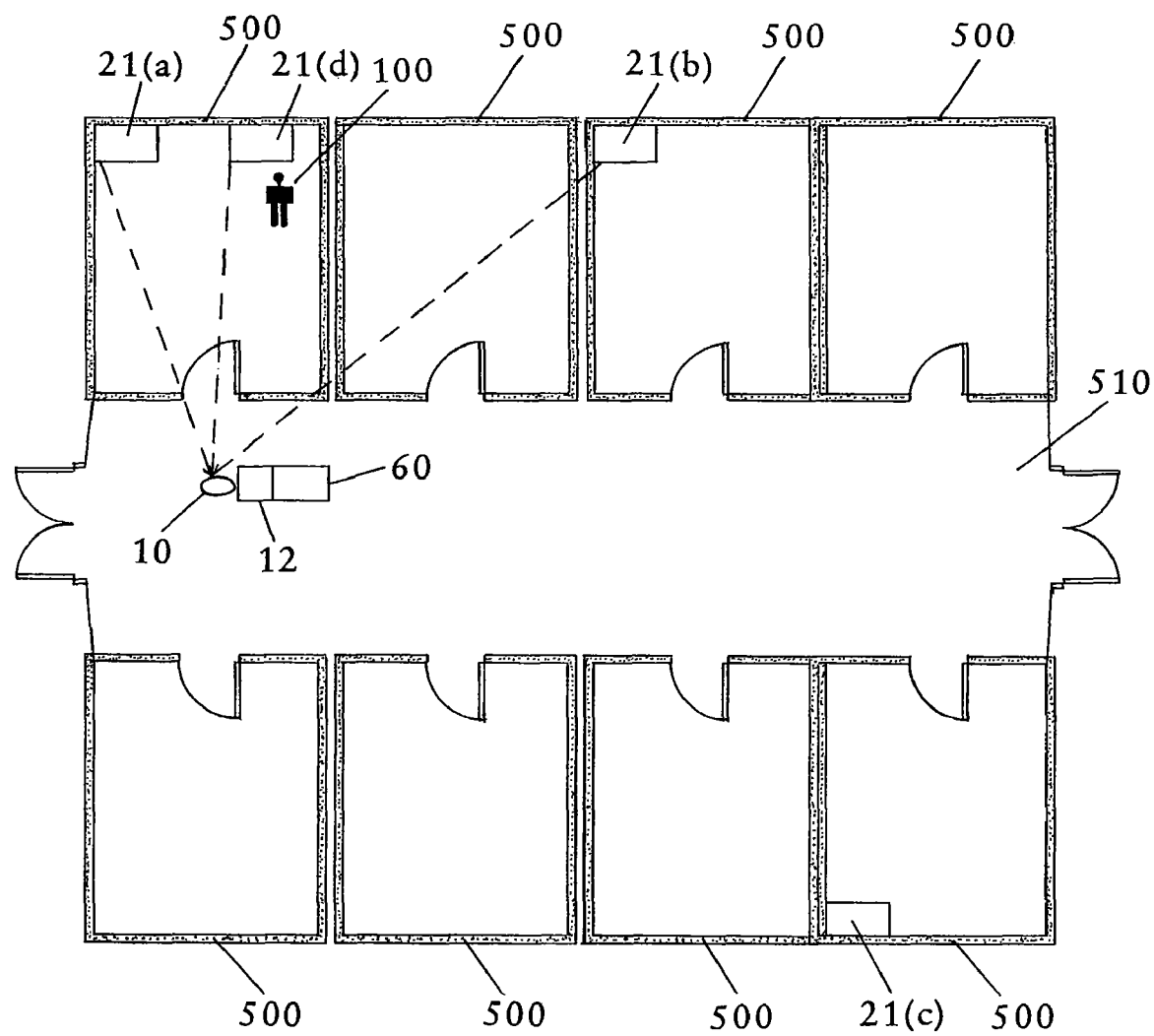
FIG. 5 is a graphical illustration of a system of determining a location of a medical device and a portable patient beacon, according to disclosed embodiments.

FIG. 5 is a graphical illustration of a system of determining a location of a medical device and a portable patient beacon, according to disclosed embodiments. The receiver 10, at medical device 60, receives signals from the beacons 21(*a*) and 21(*b*) located in various rooms 500. Beacon 21(*c*), located in another room 500 is not in range of the receiver 10 and, thus, the signal transmitted therefrom is not received by the receiver 10. As described above, the transceiver 12 sends the received signals from beacons 21(*a*) and 21(*b*) to the server 30 (not shown). Processor 90 triangulates the location of the receiver 10, and thus the location of the medical device 60, using the measured signal strengths and the predetermined unique IDs coded in the signals transmitted by beacons 21(*a*) and 21(*b*). As shown in the embodiment illustrated in FIG. 5, processor 90 would determine the location of the receiver 10 (and the medical device 60) located in hallway 510 to be closer to beacon 21(*a*), since the signal strength transmitted therefrom is stronger, with respect to the signal strength transmitted from the more distant beacon 21(*b*).

Thereafter, according to certain embodiments, processor 90 deduces the location of the portable patient beacon 21(*d*), and thus the location of the patient 100, as being in close proximity the medical device 60, since the receiver 10 receives a signal from the portable patient beacon 21(*d*).

As noted above, according to certain embodiments the portable patient beacon 21(*d*) may be adjusted to transmit a reduced-power signal to limit its range, thereby providing improved localization of the patient 100. In this case, the portable patient beacon 21(*d*) may transmit at a power such that the receiver 10 would only detect a signal therefrom when in the same room 500, for example, as the portable patient beacon 21(*d*). Once the location of the receiver 10 is determined, if the receiver 10 receives a signal from the portable patient beacon 21(*d*), the location of the portable patient beacon 21(*d*) would be determined to be within the same room 500 as the receiver 10. As a result, the location of the patient 100 would be deduced, with acute spatial resolution, as being within the same room 500 as well.

Embodiments disclosed herein provide a method and system for efficiently locating valuable devices and equipment in an environment where they can be misplaced or lost. As a result of locating the needed devices and equipment, patients located proximate to the devices and equipment may be quickly found in order to provide them care. The disclosed methods and systems require minimal installation and modification relative to the conventional methods and systems in place to provide similar features.

As opposed to conventional systems, according to certain embodiments disclosed herein, the item(s) (e.g., a medical device) to be located are attached to or near a receiver and a transceiver that sends respective signals received from one or more beacon transmitters to a centralized processor that determines the location of the item(s). Therefore, fixed installation of antennae and/or IR detectors throughout a facility, in order to detect signals from the item(s) to be located, is unnecessary. Instead, relatively inexpensive beacon transmitters, which are easily transferable and reconfigurable, may be employed such that the beacon transmitters may be located in virtually any location throughout a facility. As a result of the systems and methods disclosed herein, it is possible for the item(s) to be located to send signals used to determine the actual location thereof, as opposed to fixed points (e.g., fixed antennae) in a facility sending signals to a centralized processor merely indicating where the item(s) have passed through.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of determining a location of a medical device, comprising:
    receiving, over a first communication connection, one or more signals at the medical device transmitted by one or more beacons, respectively, at known locations;
    sending, over a second communication connection different from the first communication connection, from the medical device the received one or more signals to a processor; and
    determining, by the processor, the location of the medical device based on the received one or more signals.

2. The method of claim 1, wherein each of the one or more signals transmitted by the one or more beacons, respectively, are coded with a unique ID.

3. The method of claim 2, wherein the determining comprises:
    when a plurality of signals are received at the medical device, measuring a signal strength of each of the plurality of received signals; and
    triangulating the location of the medical device based on the measured signal strengths and the unique IDs of each of the plurality of received signals.

4. The method of claim 2, wherein the determining comprises:
    if a plurality of signals are received at the medical device, triangulating the location of the medical device based and the respective unique IDs of each of the plurality of received signals.

5. The method of claim 1, further comprising:
    receiving, over the first communication connection, a signal at the medical device transmitted by a portable patient beacon;
    sending, over the second communication connection, the received signal transmitted by the portable patient beacon to the processor; and
    determining, by the processor, a location of the portable patient beacon, based on the determined location of the medical device.

6. The method of claim 1, wherein all of the one or more beacons transmit using the same frequency.

7. The method of claim 1, wherein the one or more beacons are portable such that the relative positioning of the one or more beacons is reconfigurable.

8. The method of claim 1, further comprising periodically powering up a receiver at the medical device and sending currently received signals transmitted by one or more beacons to the processor.

9. The method of claim 1, further comprising recording determined locations of the medical device.

10. The method of claim 5, further comprising reducing a strength of the signal transmitted by the portable patient beacon to limit a range thereof.

11. A system for determining a location of a medical device, comprising:
   one or more transmitting units at known locations to transmit one or more signals, respectively;
   a receiver at the medical device to receive the one or more signals over a first communication connection; and
   a transceiver, communicatively coupled to the receiver, to send the received one or more signals to a processor over a second communication connection different from the first communication connection, the processor determining the location of the medical device based on the received one or more signals.

12. The system of claim 11, wherein each of the one or more signals transmitted by the one or more transmitting units, respectively, are coded with a unique ID.

13. The system of claim 12, wherein the processor is configured to:
   when a plurality of signals are received by the receiver, measure a signal strength of each of the plurality of received signals; and
   triangulate the location of the medical device based on the measured signal strengths and respective unique IDs of each of the plurality of received signals.

14. The system of claim 12, wherein the processor is configured to, if a plurality of signals are received at the receiver, triangulate the location of the medical device based on the respective unique IDs of each of the plurality of received signals.

15. The system of claim 11, further comprising:
   a portable patient beacon to transmit a signal received by the receiver, wherein the transceiver sends the signal to the processor, over the second communication connection, to determine a location of the portable patient beacon, based on the determined location of the medical device.

16. The system of claim 11, wherein all of the one or more transmitting units are configured to transmit using the same frequency.

17. The system of claim 11, wherein the one or more transmitting units are portable such that the relative positioning of the one or more transmitting units is reconfigurable.

18. The system of claim 11, wherein the receiver is configured to periodically power up and communicate with the transceiver to send currently received signals transmitted by one or more transmitting units to the processor.

19. The system of claim 11, further comprising a memory configured to record determined locations of the medical device.

20. The system of claim 15, wherein a strength of the signal transmitted by the portable patient beacon is reducible to limit a range thereof.

21. An apparatus for determining a location of one or more items within an institution, comprising:
   one or more beacons at known locations transmitting one or more signals, respectively;
   a receiver at an item receiving the one or more signals over a first communication connection;
   a transceiver sending the received one or more signals to a processor over a second communication connection different from the first communication connection, the processor determining the location of the item based on the received one or more signals; and
   a portable patient beacon transmitting a signal received by the receiver, wherein the transceiver sends the signal transmitted by the portable patient beacon to the processor to determine a location of the portable patient beacon, based on the determined location of the item.

* * * * *